US00PP17270P2

(12) United States Plant Patent
Rysselberghe

(10) Patent No.: US PP17,270 P2
(45) Date of Patent: Dec. 12, 2006

(54) ***PHALAENOPSIS* PLANT NAMED 'ATLANTIS'**

(50) Latin Name: ***Phalaenopsis* sp.**
Varietal Denomination: Atlantis

(75) Inventor: Ronie van Rysselberghe, Lochristi (BE)

(73) Assignee: Microflor NV, Lochristi (BE)

( * ) Notice: Subject to any disclaimer, the term of this patent is extended or adjusted under 35 U.S.C. 154(b) by 74 days.

(21) Appl. No.: 11/037,608

(22) Filed: Jan. 18, 2005

(51) Int. Cl.
*A01H 5/00* (2006.01)

(52) U.S. Cl. ..... Plt./311

(58) Field of Classification Search ..... Plt./311
See application file for complete search history.

*Primary Examiner*—Kent Bell

(57) ABSTRACT

A new cultivar of *Phalaenopsis* plant named 'Atlantis' that is characterized by broad elliptic dull green leaves and free flowering purple flowers.

1 Drawing Sheet

Botanical classification: *Phalaenopsis* sp.
Variety denomination: 'Atlantis'.

BACKGROUND OF THE INVENTION

The present invention relates to a new and distinct cultivar of *Phalaenopsis* plant botanically known as *Phalaenopsis* sp. and hereinafter referred to by the cultivar name 'Atlantis'.

The new cultivar is the product of a breeding program conducted by the inventor in a cultivated area of Lochristi, Belgium.

'Atlantis' is a hybrid that originated from the hybridization of the female or seed parent a proprietary *Phalaenopsis* identified as 'JPH00150' (not patented) and the male or pollen parent a proprietary *Phalaenopsis* identified as 'JPH00423' (not patented). The cultivar 'Atlantis' was selected by the inventor in May of 1999 as a single plant within the progeny of the stated cross in Lochristi, Belgium.

Asexual reproduction by tissue culture of the new cultivar 'Atlantis' was first performed in May of 1999 in Lochristi, Belgium. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Phalaenopsis* cultivar 'Atlantis'. These traits in combination distinguish 'Atlantis' as a new and distinct cultivar.

1. *Phalaenopsis* 'Atlantis' exhibits broad elliptic leaves.
2. *Phalaenopsis* 'Atlantis' exhibits flowers that are primarily purple.
3. *Phalaenopsis* 'Atlantis' exhibits dull, green leaves.
4. *Phalaenopsis* 'Atlantis' exhibits free flowering.

The new cultivar 'Atlantis' is distinguishable from the female parent *Phalaenopsis* 'JPH00150' by the following characteristics:

1. 'Atlantis' has darker purple flowers.

The new cultivar 'Atlantis' is distinguishable from the male parent *Phalaenopsis* 'JPH00423' by the following characteristics:

1. 'Atlantis' has darker purple flowers.

The closest comparison cultivar is *Phalaenopsis* 'Artemis'. The new cultivar *Phalaenopsis* 'Atlantis' differs from 'Artemis' by the following characteristics:

1. 'Atlantis' has better resistance against root diseases.
2. 'Atlantis' has petals with a dark labellum whereas the petals of 'Artemis' are uniformly colored.
3. 'Atlantis' has petals that are colored purple 78A whereas the petals of 'Artemis' are 78B to 78C.

BRIEF DESCRIPTION OF THE DRAWING

The accompanying photograph illustrates the distinguishing traits of *Phalaenopsis* 'Atlantis'. The plant in the photograph shows an overall view of a 55 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Phalaenopsis* cultivar named 'Atlantis'. Data was collected in Lochristi, Belgium from 55 week old greenhouse grown plants in 12 centimeter containers. The time of year was Fall. The average temperature during the first 25 weeks was 25° Centigrade. The average temperature during the next 4 weeks was 18° Centigrade. The average temperature during the last weeks was 20° Centigrade.

The light level was natural outdoor light and there were no photoperiodic treatments or growth retardants used. Color determinations are in accordance with The Royal Horticultural Society Colour Chart 2001 edition, except where general color terms of ordinary dictionary significance are used. The growing requirements are similar to the species. 'Atlantis' has not been tested under all possible conditions and phenotypic differences may be observed with variations in environmental, climatic, and cultural conditions, however, without any variance in genotype.

Botanical classification: *Phalaenopsis* sp. 'Atlantis'.
Parentage: 'Atlantis' is a hybrid plant that resulted from the hybridization of the following parent plants:
*Female parent.*—*Phalaenopsis* sp. 'JPH00150'.
*Male parent.*—*Phalaenopsis* sp. 'JPH00423'.
Vigor: Moderate.
Growth rate: Moderate.
Growth habit: Upright.
Plant shape: Monopodial with basal rosette and flowering stems growing from leaf-axils.
Suitable container size: 12 cm container.
Height to top of flowers: Average 39.5 cm. in height.
Height to top of leaves: Average 16 cm. in height.
Width: Average 25 cm. in width.
Hardiness: USDA Zone 11.
Propagation: Tissue culture.
Time to initiate roots summer. Approximately 28 days to produce roots on an initial cutting at 24° Centigrade.
Time to initiate roots winter: Approximately 42 days to produce roots on an initial cutting at 24° Centigrade.
Time to produce a rooted cutting or liner summer: Approximately 168 days at 24° Centigrade.
Time to produce a rooted cutting or liner winter: Approximately 270 days at 24° Centigrade.
Root system: Fleshy, rounded, slightly glossy, average diameter 5 mm.
Foliage:
*Texture.*—Smooth, glossy, slightly furrowed.
*Leaf arrangement.*—Distichous.
*Quantity of leaves per plant.*—4.
*Leaf shape.*—Obovate.
*Leaf apex.*—Unequal Acute.
*Leaf base.*—Cuneate.
*Leaf length.*—Average 15.8 cm. in length.
*Leaf width.*—Average 6.3 cm. in width.
*Pubescence.*—Absent.
*Leaf margin.*—Entire.
*Vein pattern.*—Camptodromous.
*Young leaf color* (*upper surface*).—Varies from 137A to 146A to 146B.
*Young leaf color* (*lower surface*).—Between 146A and 146B.
*Mature leaf color* (*upper surface*).—Varies from 137A to 147A.
*Mature leaf color* (*lower surface*).—146A.
*Vein color* (*lower surface*).—Varies from 137A to 147A.
*Vein color* (*upper surface*).—146A.
*Durability of foliage to stress.*—High.
Flower:
*Flower arrangement.*—Axillary raceme.
*Inflorescence type.*—Raceme.
*Inflorescence dimensions.*—Average 11.6 cm. in diameter and 48.5 cm. in length.
*Flowering habit.*—Continuously once a year.
*Flower form.*—Zygomorphic.
*Quantity of flowers per inflorescence.*—Average 8.
*Quantity of flower stems per plant.*—Average 2.
*Quantity of flowers and buds per plant.*—Average 16.
*Flowering season.*—Late fall to spring.
*Time to flower or response time.*—6 months.
*Rate of flower opening.*—Lowest flowers of the raceme open first, all flowers will open in approximately 21 days.
*Fragrance.*—None.
*Self-cleaning or persistent.*—Self-cleaning.
*Flower bud length.*—9 mm. in length.
*Flower bud diameter.*—7 mm. in diameter.
*Flower bud shape.*—Broad ovate.
*Bud color.*—148A tinged with 177B.
*Rate of bud opening.*—14 days.
*Flower aspect.*—Outward.
*Flower shape.*—Zygomorphic.
*Flower dimensions.*—8.1 cm. in diameter and 3.1 cm. in height.
*Flower longevity.*—Lasts at least 28 days on plant.
*Petal appearance.*—Dull.
*Petal texture.*—Glabrous.
*Petal arrangement.*—One petal one each side of the column.
*Number of petals.*—Two in number.
*Petals fused or unfused.*—Unfused.
*Petal shape.*—Reniform.
*Petal margin.*—Entire.
*Petal apex.*—Rounded.
*Petal dimensions.*—4 cm. in length and 4.6 cm. in width.
*Petal color when opening* (*upper side*).—N78A.
*Petal color when opening* (*under side*).—N78B to N78C.
*Petal color when fully opened* (*upper side*).—N78A to N78B.
*Petal color when fully opened* (*under side*).—N78C.
*Petal color fading to.*—N80A.
*Labellum appearance.*—Glabrous, dull.
*Labellum arrangement.*—Lobed.
*Labellum shape.*—Lobed, outward lobes broad obovate, middle lobe deltoid.
*Labellum tip.*—Cleft into two curled, linear projections.
*Labellum dimensions.*—Average 2.8 cm. in length and 2.6 cm. in width.
*Labellum color, young, upper side.*—N78A, striped 76D.
*Labellum color, young, lower side.*—N78B.
*Labellum color, mature, upper side.*—N78A, striped 76D.
*Labellum color, mature, lower side.*—N78B.
Callosities:
*Callositie location.*—At the base of the central lobe of the labellum and between the lateral lobes.
*Callositie dimensions.*—Average 5 mm in length and 3 mm in width.
*Callositie color, young.*—13B, dotted N79B.
*Callositie color, mature.*—13B, dotted N79B.
Sepals:
*Sepal appearance.*—Dull, glabrous.
*Sepal arrangement.*—Two lateral sepals and one dorsal sepal.
*Number of sepals.*—Three in number.
*Sepal shape.*—Broad elliptic.
*Sepal margin.*—Entire.
*Sepal tip.*—Rounded.
*Sepal base.*—Attenuate.
*Lateral sepal length.*—Average 4.1 cm.
*Dorsal sepal length.*—Average 4.2 cm.
*Lateral sepal width.*—Average 2.7 cm.
*Dorsal sepal width.*—Average 3 cm.
*Lateral sepal color, immature, upper surface.*—N78B with a base 76C to 76D with dots N79B.

*Dorsal sepal color, immature, upper surface.*—N78A to N78B with dots 76C to 76D.

*Lateral sepal color, immature, under surface.*—N78B.

*Dorsal sepal color, immature, under surface.*—N78B.

*Lateral sepal color, mature, upper surface.*—N78B with a base 76C to 76D with dots N79B.

*Dorsal sepal color, mature, upper surface.*—N78A to N78B with dots 76C to 76D.

*Lateral sepals color, mature, under surface.*—N78B.

*Dorsal sepal color, mature, under surface.*—N78B.

Peduncle:

*Peduncle dimensions.*—Average 48.5 cm. in length and 4 mm. in diameter.

*Peduncle angle.*—40° from vertical.

*Peduncle color.*—Between 147A and N200A with yellow-green dots 146A to 146B.

*Peduncle strength.*—Strong.

Pedicels:

*Pedicel dimensions.*—Average 3.4 cm. in length and 3 mm. in diameter.

*Pedicel angle.*—85° from vertical.

*Pedicel color.*—177A.

*Pedicel strength.*—Moderate to strong.

Reproduction organs:

*Column dimensions.*—Average 9 mm in length and 6 mm in width.

*Column color.*—N78C.

*Pollinia quantity.*—Moderate.

*Pollinia diameter.*—1 mm.

*Pollinia color.*—23A.

*Stigma shape.*—Rounded concave.

*Stigma color.*—76B to 76C.

*Stigma dimensions.*—5 mm in length and 5 mm in width.

*Ovary color.*—77C to 77D.

*Ovary dimensions.*—8 mm in length and 2 mm in diameter.

Seed: Seed production has not been observed.

Disease resistance: Plants of the new *Phalaenopsis* are resistant to root diseases.

Pest resistance: Plants of the new *Phalaenopsis* have not been observed for pest resistance.

It is claimed:

1. A new and distinct variety of *Phalaenopsis* plant named 'Atlantis' as described and illustrated.

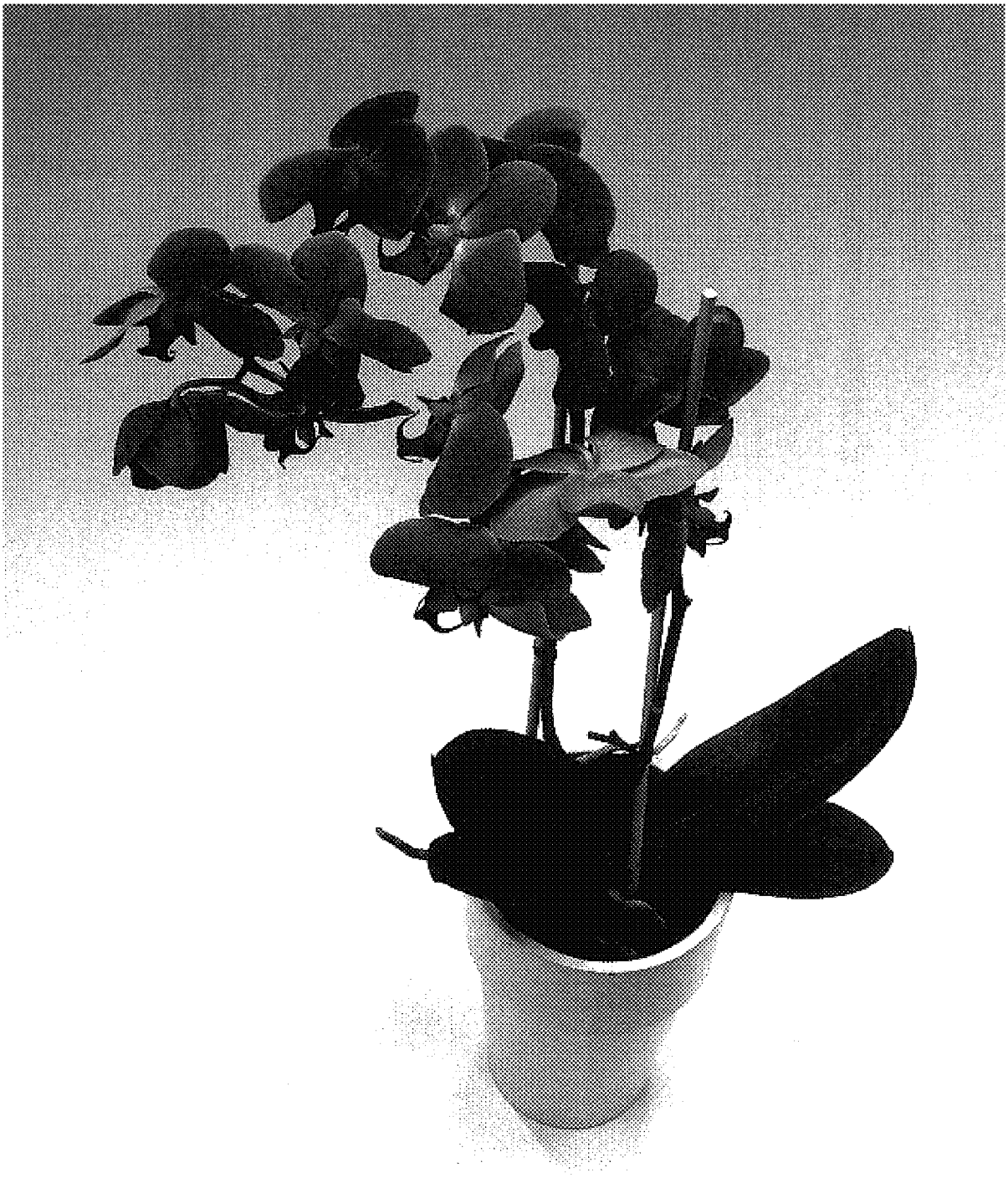

* * * * *